(12) United States Patent
Bissonnette et al.

(10) Patent No.: US 6,923,039 B2
(45) Date of Patent: Aug. 2, 2005

(54) METHOD AND APPARATUS FOR TESTING GOLF BALLS

(75) Inventors: Laurent Bissonnette, Portsmouth, RI (US); Emanuel Vieira, New Bedford, MA (US)

(73) Assignee: Acushnet Company, Fairhaven, MA (US)

( * ) Notice: Subject to any disclaimer, the term of this patent is extended or adjusted under 35 U.S.C. 154(b) by 3 days.

(21) Appl. No.: 10/676,828

(22) Filed: Oct. 3, 2003

(65) Prior Publication Data

US 2005/0072209 A1 Apr. 7, 2005

(51) Int. Cl.$^7$ .................................................. G01N 3/30
(52) U.S. Cl. ..................................... 73/12.02; 73/65.03
(58) Field of Search ............................. 73/12.01, 12.02, 73/12.04, 12.09, 12.11, 65.03

(56) References Cited

U.S. PATENT DOCUMENTS

| | | | | |
|---|---|---|---|---|
| 5,672,809 A | * | 9/1997 | Brandt ....................... | 73/12.01 |
| 6,571,600 B2 | * | 6/2003 | Bissonnette et al. ....... | 73/12.02 |
| 6,585,605 B2 | * | 7/2003 | Erickson et al. ............ | 473/282 |

* cited by examiner

*Primary Examiner*—Max Noori
(74) *Attorney, Agent, or Firm*—Kristin D. Wheeler

(57) ABSTRACT

A method and an apparatus for measuring coefficient of restitution of an impact are disclosed. The apparatus includes a launching device, an enclosure, a second initially stationary object, and a plurality of speed sensors. The launching device causes a first object to be moved toward the second object and to impact the second object within the enclosure. The sensors are positioned within the enclosure to determine the velocity of the first object before impact, the velocity of the second object after impact and optionally the velocity of the first object after impact. Using these velocities, the coefficient of restitution of the impact can be determined. By using an enclosure and a second object that is initially stationary and is moved upon impact, the coefficient of restitution of the first object can be determined. The apparatus closely simulates a real-world golf ball/golf club collision. The first object may simulate a golf ball or a golf ball core assembly and the second object may simulate a golf club, and vice versa.

The apparatus may also continually and automatically return the second object to its initial, pre-impact position, and the apparatus may be used to determine the durability of golf balls by repeatedly impacting golf balls against the second object.

23 Claims, 3 Drawing Sheets

METHOD AND APPARATUS FOR TESTING GOLF BALLS

TECHNICAL FIELD OF INVENTION

The present invention generally relates to a method and an apparatus for measuring coefficient of restitution between two colliding objects, and more particularly for measuring the coefficient of restitution of an impact between a golf ball and a simulated golf club. The present invention is also directed to a method and an apparatus for determining the durability of golf balls.

BACKGROUND OF THE INVENTION

Golf ball designers are interested in determining various aerodynamic and mechanical characteristics for golf balls. One such characteristic indicative of golf ball performance is the coefficient of restitution (CoR) from impacting golf clubs. The coefficient of restitution is the ratio of the relative velocity between two objects after direct impact to the relative velocity before impact. As a result, the CoR can vary from 0 to 1, with 1 being equivalent to a perfectly or completely elastic collision and 0 being equivalent to a perfectly plastic or completely inelastic collision. Since a ball's CoR directly influences the ball's initial velocity after club collision and travel distance, manufacturers are interested in this characteristic for designing and testing golf balls.

One conventional technique for measuring CoR uses a golf ball or golf ball subassembly, air cannon, and a stationary vertical steel plate. The steel plate provides an impact surface weighing about 100 pounds or about 45 kilograms. A pair of ballistic light screens, which measure ball velocity, are spaced apart and located between the air cannon and the steel plate. The ball is fired from the air cannon toward the steel plate over a range of test velocities from 50 ft/s to 180 ft/sec. As the ball travels toward the steel plate, it activates each light screen so that the time at each light screen is measured. This provides an incoming time period proportional to the ball's incoming velocity. The ball impacts the steel plate and rebounds though the light screens, which again measure the time period required to transit between the light screens. This provides an outgoing transit time period proportional to the ball's outgoing velocity. The coefficient of restitution can be calculated by the ratio of the outgoing transit time period to the incoming transit time period. A drawback of this method is that the 45 kg steel plate is a poor simulation of a 200 gram golf club.

A CoR measuring method employed by the U.S.G.A. uses a golf ball or golf ball subassembly, a launching device, and a substantially fixed titanium disk. The titanium disk intending to simulate a golf club is circular, and has a diameter of about 4 inches, and has a mass of about 200 grams. The disk is mounted on an X-Y-Z table so that its position can be adjusted relative to the launching device prior to testing. A pair of ballistic light screens are spaced apart and located between the launching device and the titanium disk. The ball is fired from the launching device toward the titanium disk at a predetermined test velocity. As the ball travels toward the titanium disk, it activates each light screen so that the time period to transit between the light screens is measured. This provides an incoming transit time period proportional to the ball's incoming velocity. The ball impacts the titanium disk, and rebounds through the light screens which measure the time period to transit between the light screens. This provides an outgoing transit time period proportional to the ball's outgoing velocity. The CoR can be calculated using the mass of the ball, the mass of the disk, outgoing time difference and incoming time difference.

The U.S.G.A. method also has drawbacks. In order to obtain useful data, the ball must impact the titanium disk at its center. Due to the size of the disk and the inaccuracy of the air cannon, the location of the titanium disk on the X-Y-Z table must be adjusted by trial and error until the ball impacts the plate at the center. Since the air cannon is inconsistent, many shots miss the center of the disk and are rejected. Furthermore, examination of the disk and ball impact position is time consuming, and numerous shots are required to obtain a statistically significant population of central impacts to determine the CoR. This required set-up is time consuming and undesirable.

Therefore, a need exists for a method and apparatus for measuring the CoR of a golf ball after a collision with a simulated club that reflect the actual mechanics of the real-world golf swing, as closely as possible. This method also preferably minimizes potential problems with aiming the ball at a relatively small-simulated club.

SUMMARY OF THE INVENTION

Broadly, the present invention comprises a method and an apparatus for measuring the coefficient of restitution of a golf ball.

The present invention is also broadly directed to a method and an apparatus for testing the durability of golf balls.

The present invention is directed to a method for testing the coefficient of restitution of a golf ball comprising the steps of: positioning an impacted object in an initial position and in a stationary state in an enclosure, constraining the impacted object to movement within a predetermined path within the enclosure, moving an impacting object toward and impacting the impacted object, wherein one of either the impacting object or the impacted object is the golf ball. The method further comprises the steps of determining the pre-impact velocity of the impacting object, determining the post-impact velocity of the impacted object, and determining the coefficient of restitution of the golf ball.

In accordance to one aspect of the present invention, the impacting object is the golf ball, and the impacted object is a simulated golf club. According to another aspect of the present invention, the impacting object is a simulated golf club and the impacted object is the golf ball.

The method of measuring the coefficient of restitution may further comprise the step of automatically returning the impacted object to its initial position.

The pre-impact velocity of the impacting object and the post-impact velocity of the impacted object are determined by measuring a time period that the objects transit a predetermined distance. Additionally, the post-impact velocity of the impacting object may also be determined by measuring a time period that the object transits a predetermined distance. Alternatively, the post-impact velocity of the impacting object is determined in accordance to the principle of conversation of momentum. The coefficient of restitution is determined as the ratio between the relative velocity between the impacting object and the impacted object after impact to that before impact.

The present invention is also directed to a method for testing the durability of a golf ball comprising the steps of: (a) positioning an impacted object in an initial position and in a stationary state in an enclosure, (b) constraining the impacted object to movement within a predetermined path within the enclosure, (c) moving an impacting object at a predetermined velocity toward and impacting the impacted object, wherein one of either the impacting object or the impacted object is the golf ball, (d) automatically returning the impacted object to the initial position, and (e) repeating steps (c) and (d) until failure of the golf ball is noted.

The method of testing the durability of the golf ball may further include the step of returning the impacting object to the launching device and/or the step of providing a repositioning device to return the impacted object to its initial position.

The present invention is further directed to an apparatus for testing golf ball comprising an enclosure defining a predetermined path, an impacted object positioned in an initial position within said predetermined path, wherein the movement of the impacted object after impact is constrained within the predetermined path, and a launching device configured to launch an impacting object at a predetermined velocity to impact the impacted object, wherein one of either the impacting object or the impacted object is the golf ball.

According to one aspect of the invention, the impacting object is the golf ball, and the impacted object is a simulated golf club. According to another aspect of the invention, the impacting object is a simulated golf club and the impacted object is the golf ball. The simulated golf club may be solid or hollow with an impact face. The impact face may be flexible. The enclosure may be connected to a dampening device adapted to retain the impacted object after impact. On the other hand, the enclosure can be connected to a repositioning device associated with the impacted object to return the impacted object to the initial position after impact. The enclosure may also have a device that returns the impacting object to the launching device.

The apparatus may further comprise a first sensor for determining the pre-impact velocity of the impacting object and a second sensor for determining the post-impact velocity of the impacted object. The first and second sensors comprise a pair of break-beam sensors. The first and second sensors are operatively connected to a digital recording device, wherein the digital recording device stores the velocities measured by the sensors.

DETAILED DESCRIPTION OF THE PREFERRED EMBODIMENTS

Figure 1:
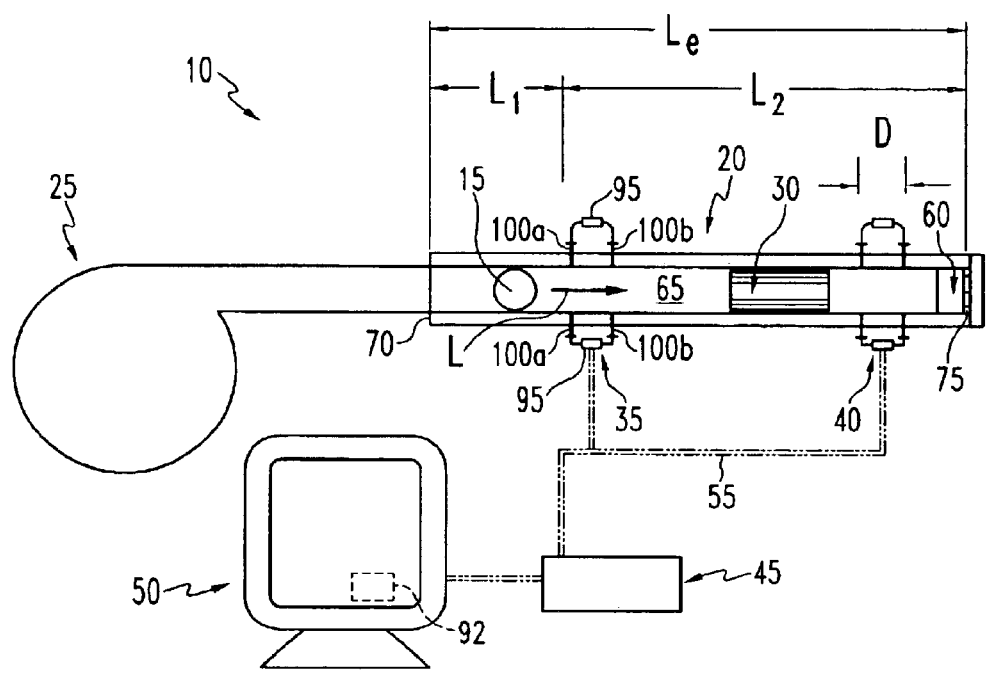
FIG. 1 is a schematic elevational view representing an apparatus for measuring a first object of the present invention.

FIG. 1 illustrates a schematic elevational view of an apparatus 10 for testing of the present invention. The apparatus 10 is adapted for use with a first object 15, which in this embodiment is a golf ball. The first object 15, however, can be any object that coefficient of restitution data is required. Preferably, the object has a spherical shape and may be selected from the following group including golf balls, golf ball subassemblies, tennis balls, baseballs, and softballs. As used herein, the term golf ball includes golf ball and golf ball assemblies.

Golf ball subassembly means any object that forms a portion of a golf ball. For example, a golf ball subassembly can be a molded single or multiple-piece core or a fluid filled center. A golf ball subassembly can also be a core comprised of a center and another layer formed by molding or winding tensioned elastic thread thereon. A golf ball subassembly may further include a core with one or more intermediate layers or cover formed on the core as known by one of ordinary skill in the art.

The apparatus 10 includes an enclosure 20, a launching device 25, a second object 30, sensor assemblies 35 and 40, a data acquisition card 45, a computer 50, various cables 55, and a dampening device 60. As used herein, the "first object" indicates the impacting object and the "second object" indicates the impacted object.

The enclosure 20 defines a longitudinally extending chamber 65 for receiving the first and second objects 15 and 30. The enclosure 20 is configured and dimensioned to allow the first and second objects 15 and 30 to move without substantial resistance along the longitudinal axis of chamber 65, but also constraining the movement of the objects so that it is primarily in the longitudinal direction. Preferably, an inner diameter of the enclosure 20 is greater than the outer diameter of the first object and the outer diameter of the second object by about 0.01–0.05 inch clearance.

By way of non-limiting example, the first object may be a golf ball with an outer diameter of 1.68 inches. The second object may be a cylindrical slug with an outer diameter of 1.79 inches. The associated enclosure may have an inner diameter of about 1.80 inches or higher.

The enclosure 20 is preferably a cylindrical tube with a first end 70 and a second end 75. The enclosure 20 has a circular cross-sectional area; however, the present invention is not limited to this shape. The first end 70 is open and is operatively associated with the launching device 25 so that the first object 15, which begins in the launching device, upon actuation can move into chamber 65 along a longitudinal direction L. The second end 75 is preferably vented and may include an optional dampening system 60. Damper 60 may be spring damper, an air damper or a hydraulic damper. Damper 60's primary function is to capture and retain second and/or first objects after ejection from enclosure 20. A suitable damper 60 is the SAS 1.5×1 PS-04, available from the EFDYN, Inc. in Tulsa, Okla. If the dampening system is not used and the second end 75 is open, it is preferred that a device, such as protective netting, be positioned downstream of the enclosure 20 to catch the second and/or first objects after impact.

Figure 2:
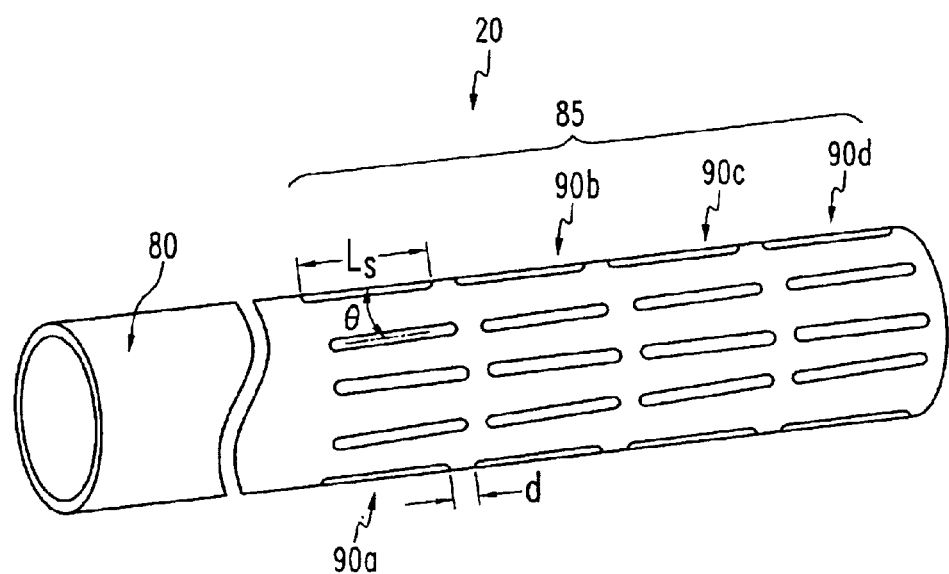
FIG. 2 is a perspective view of an enclosure for use in the apparatus of FIG. 1.

The total length $L_e$ of the enclosure 20 is preferably sufficient (i) to allow the velocity of the first object 15 to be measured prior to impact and optionally after impact with the second object 30, (ii) to allow the second object 30 to move after impact to simulate a real-world club/ball collision, and (iii) to allow the velocity of the second object 30 to be measured after impact. Referring to FIGS. 1 and 2, the enclosure 20 further includes a first portion 80 and a second portion 85. The first portion 80 is continuous and preferably non-perforated, and has a first length $L_1$. The second portion 85 is discontinuous and preferably perforated or vented, and has a second length $L_2$. Preferably, the perforation portion 85 extends at least from a point just before impact with the second object 30 to a point just after impact with the second object 30. More preferably, the first length $L_1$ is substantially less than the second length $L_2$. Most preferably, the first length $L_1$ is 25% of the enclosure length and the second length $L_2$ is 75% of the enclosure length. In a preferred embodiment, the enclosure length $L_e$ is about 16 inches; the first length is about 4 inches, and the second length is about 12 inches.

In the perforation portion 85, the enclosure 20 defines a plurality of slots 90a–d, as shown in FIG. 2. The slots 90a–d are longitudinally spaced from one another by a distance d, which is preferably about 0.75 inches in the present embodiment. The length of each slot $L_s$, preferably, is about 1 inch. The slots are also circumferentially spaced from one another, preferably by an angle Θ of about 45° C. The slots are preferably milled into the enclosure 20. In the preferred embodiment, there are about 9 or 10 circumferential lines of slots and about eight slots in each circumferential line. Although the slots are shown as elongated, the slots can have any geometry and any number of slots can be used, so long as the slots provide the necessary air ventilation so that the first and second objects 15 and 30 experience minimal air resistance during testing.

In the preferred embodiment, the material of the enclosure 20 is metal. More preferably, the material of the enclosure 20 is stainless steel. The present invention, however, is not limited to these materials.

Referring again to FIG. 1, the launching device 25 is set-up adjacent the first end 70 of the enclosure 20. A frame may be provided for supporting launching device 25 and adjusting its position. The launching device 25 is capable of independently controlling the initial velocity and direction of the first object 15 along a flight path. Preferably launching device 25 launches the first object 15 in a substantially linear flight path shown by arrow L in FIG. 1. The preferred launching device is pneumatically powered, such as commercially available air cannon.

Figure 3:
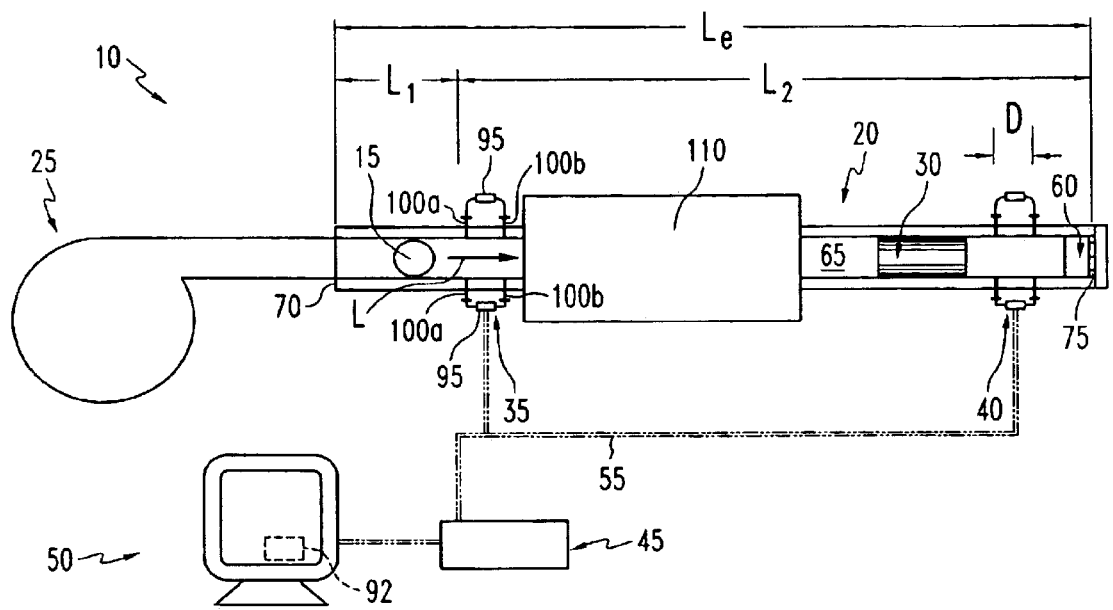
FIG. 3 is a schematic elevational view of an alternative embodiment of the apparatus of FIG. 1.

When an air cannon launching device is used, enclosure 20 optionally may have enlarged portion 110 disposed within the enclosure, as shown in FIG. 3. A purpose of the enlarged section 110 is to allow the air propelling first object 15 to vent prior to impact, so that this air would not affect the velocities of the first and second objects after impact. Additionally, the first portion 80 of enclosure 20 may also be perforated or be constructed from wire frame to vent the propelling air from the air cannon.

Preferably, the launching device 25 moves the first object 15 at a speed between about 50 ft/s and about 250 ft/s. More preferably, the launching device 25 moves the first object 15 at a speed between about 100 ft/s and about 200 ft/s, and most preferably from about 120 ft/s to about 180 ft/s.

The second object 30 is operatively associated with the enclosure 20 so that it is capable of freely moving in the direction L upon impact with the first object 15. In the present embodiment, the second object 30 is freely slidable within the enclosure 20. The second object 30 is preferably a solid cylinder as shown in FIG. 4(a). The present invention is not limited to this shape and the second object can be any shape that compliments the shape of the enclosure 20. The second object can include portions with different diameters so that the second object has stepped cylindrical portions. Second object 30 may also be hollow, as shown in FIG. 4(b). Alternatively, second object 30 may also have a flexible impact face, e.g., a face with a weakened section surrounding a center portion, as illustrated in FIG. 4(c) to simulate a driver club with a flexible face.

The first object 15 is preferably spherical and weighs about 1 ounce to about 5 ounces. More preferably, the first object 15 is a regulation dimpled golf ball.

The second object 30 is preferably metal. More preferably, the second object 30 is titanium. Specifically, the preferred material is commercially available 6A1 4V Grade 5 titanium. The present invention, however, is not limited to these materials. Since the second object 30 in the preferred embodiment simulates a golf club, the preferred mass of the second object 30 is that of the golf club. More specifically, the preferred mass of the second object is between about 100 grams and about 500 grams. Most preferably, the mass of the second object 30 is between about 180 grams and about 250 grams.

Two sensor assemblies 35 and 40 are coupled to the enclosure 20, and are preferably in communication with a computer 50 as discussed below. The sensors 35 and 40 are longitudinally spaced apart. The sensor assemblies 35 and 40 comprise at least two proximity sensors spaced a distance D greater than one inch and more preferably greater than about three inches. These assemblies are positioned so that the first velocity of the first object 15 can be determined prior to impacting the second object 30, and the second velocity of the second object 30 can be determined after being impacted by the first object 15.

Preferably, the sensors 35, 40 are non-contact sensors such as break-beam sensors. The sensors initiate and terminate various system functions, as discussed below. One such function is to act as a timer actuator for starting and stopping a timer 92 (shown in phantom in FIG. 1). The present invention, however, is not limited to this type of actuation device. Other devices such as a light screen assembly, proximity sensors, or a series of laser beams can also be used.

In the preferred embodiment, the first sensor assembly 35 includes two fiberoptic sensors 95 and a pair of photoelectric sensors 100a, 100b operatively connected to each fiberoptic sensor and spaced a known distance apart. The second sensor assembly 40 is similarly configured. Suitable fiber-optic sensors are commercially available from Omron Sensors in Schaumberg, Ill., under part number E32-TC200. Suitable photoelectric sensors are also commercially available from Omron Sensors under part number E3X-DA41-N. When the first object 15 passes sensors 100a, the timer 92 is actuated. When the first object 15 passes sensors 100b, the timer 92 is stopped. Knowing the distance between the sensors 100a and 100b, a first velocity of the first object can thus be calculated from the time period to transit between sensors 100a and 100b according to the formula below:

$$V = \frac{t_1 - t_2}{D},$$

where
V=velocity;
$t_1$=time at 100a;
$t_2$=time at 100b; and
D=known distance between 100a and 100b.

The sensor assembly 40 similarly calculates the second velocity of the second object 30 after it passes thereby. Either sensor assembly 35 or 40 may also measure the post-impact velocity of first object 15 depending on whether the first object continues to travel forward or rebounds in the opposite direction.

The fiber-optic sensors 95 of the sensor assemblies 35 and 40 are preferably in communication with the data acquisition card or interconnector 45 disposed between the sensor assemblies and the computer 50 and timer 92. These components are connected by cable 55. Suitable cable is commercially available from National Instruments in Austin, Tex., under the name Cable-R6868 and part number 182482-01.

The data acquisition card may be integrated into the computer 50 also, and the timer 92 may be separate from the computer. The data acquisition card 45 collects data from the sensor assemblies 35 and 40 for manipulation by computer 50. A commercially available data acquisition card is manufactured by National Instruments under the name Interconnector SCB-68 and part number 777145-01. The computer 50 has several algorithms and programs used by the system to make the determinations discussed below. Signals from the data acquisition card 45 are communicated to the computer 50 via cable 55.

Referring to FIG. 1, the timer or timing device 92 measures a time interval. In this embodiment, the timer 92 is within a personal computer equipped with a commercially available timer board. Suitable timer boards include those manufactured by National Instruments under the name Counter/Timer PCI-6601 and part number 777918-01. The timer 92 is linked to the data acquisition card 45. The invention is not limited to this type of timing device, for example other preferred devices are clocks and trigger devices, which are well known to those of ordinary skill in the art.

Generally, CoR can be determined when the initial velocities, the post-impact velocity of one of the impacting bodies, and the masses of the bodies are known. CoR can also be determined when the initial velocities and the post-impact velocities are known, Referring to FIGS. 1 and 3, the method of measuring CoR includes providing the enclosure 20 with at least one open end; providing a second object 30 in a stationary state at an initial position within the enclosure 20; moving the first object 15 toward the second object 30. In this embodiment, the step of moving further includes providing the launching device 25 at one end of the enclosure 20, setting the initial velocity and flight path of the first object 15 and launching the first object.

The sensor assembly 35 measures a first transit time interval of the first object 15 prior to its impact with the second object 30. Next, the first object 15 impacts the second object 30 causing it to move in the L direction. The sensor assembly 40 measures a second transit time interval of the second object 30 after this impact. After impact, the velocity of first object 15 is represented by a third transit time period, and can be measured by either the first sensor assembly 35 if it rebounds backward or by the second sensor assembly 40 if its momentum carries it forward, or it may have little or no velocity after impact depending on its pre-impact velocity and the relative masses of the first and second objects. The first, second and third transit time periods are used along with the known distance between the sensors in each assembly to determine a first velocity of the first object before impact, a second velocity of the second object after impact, and the third velocity of the first object after impact.

If the third velocity of the post-impact first object 15 is measured, then CoR is simply the relative velocity before impact divided by the relative velocity after impact, since all four velocities are known (with the pre-impact velocity of the second object being zero or stationary).

If the third velocity of the post-impact first object 15 is not measured, using the above data and applying the principle of conversion of momentum to calculate the third velocity, the CoR can be calculated using the following formula, assuming that the impact occurs substantially on a horizontal plane:

$$CoR = \left( \frac{V_{2f}}{V_{1i}} \times \frac{m_1 + m_2}{m_1} \right) - 1,$$

where
$v_{1i}$=first velocity of the first object;
$v_{2f}$=second velocity of the second object;
$m_1$=known or predetermined mass of the first object; and
$m_2$=known or predetermined mass of the second object.
Preferably, the computer 50 calculates the coefficient of restitution using the above formula, and stores the data for further statistical analysis or graphical presentation.

A readily recognized advantage of the present invention is that the impacted object, i.e., the second object 30 or simulated golf club, is movable, in contrast to the conventional CoR measuring technique where the impacted 45 kilogram plate is held stationary after impact. The movable second object 30 more closely related to the golf club, which is in motion after impact with the ball. Hence, the present invention more accurately represents the actual mechanics of a real-world golf shot.

To better simulate the real-world golf shot, according to another aspect of the present invention, the first object 15 simulates the club head, i.e., having a cylindrical shape and cross-sectional profiles shown in FIGS. 4(a)–(c) and weighs from about 100 grams to 500 grams (preferably about 200 grams), and the second object 30 is a dimpled golf ball. In this embodiment, the simulated club is moving and the ball is stationary before impact, and both the ball and simulated club are moving "forward" after impact, similar to a real-world golf club-golf ball impact. The simulated club head may assume other shapes, including irregular shapes.

Figure 4:
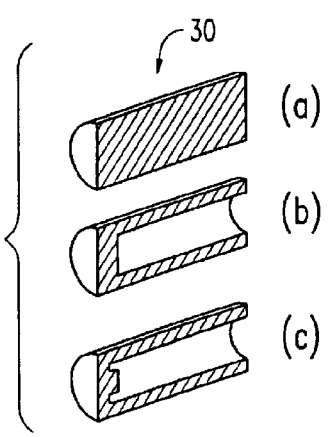
FIGS. 4(a)–(c) are cross-sectional views of three embodiments of the simulated golf clubs.

In accordance to another aspect of the invention, the advantages of a flexible face driver club can be determined with the present invention, particularly with the second object 30 shown in FIG. 4(*c*). In this embodiment, the flexibility of the driver face contributes to the CoR of the impact, and the present invention can estimate this contribution by comparing the impacts with non-flexible second objects 30 to impacts with flexible second objects 30, when all other parameters are kept the same.

In accordance to another aspect of the present invention, instead of being a dampening device, device 60 can be a repositioning device, as shown schematically in FIGS. 1 and 3. Suitable repositioning devices can be a rod-and-piston mechanism, a rod-and-rotating wheel mechanism, a pneumatically controlled rod, or the like, as long as the device is capable of catching and returning the second object 30 to its initial, pre-impact position in enclosure 20. Repositioning device may also include a magnetic or magnetized sleeve fitted concentrically outside of enclosure 20 that can move second object 30, preferably made from a ferrous material, automatically back to its initial, pre-impact position. The magnetic or magnetized sleeve can be driven by any of the positioning mechanism listed above.

Additionally, repositioning device 60 may be a helical coil spring that absorbs sufficient kinetic energy from the impacted second object 30 to return the second object 30 to its initial, pre-impact position. The appropriate spring constant of the spring can be determined by the mass and velocity of the impacted second object, the distance that the second object must travel to return to the initial position and the coefficient of friction between the second object and the enclosure 20. Alternatively, repositioning device 60 may include an upwardly curved section terminating with a dampening device that converts some of the kinetic energy of the impacted second object to potential energy. Thereafter, the second object is allowed to slide down the curved section to return to the initial, pre-impact position. The vertical height of the curved section necessary to return the second object can be determined from the mass of the second object, the distance that the second object must travel to return to the initial position and the coefficient of friction between the second object and the enclosure 20. Excess velocity from the impacted second object 30 can be absorbed by the damper. Preferably, enclosure 20 includes a stopper, such as an o-ring disposed on the inside wall of enclosure 20, to ensure that second object 30 does not travel beyond the initial position.

In this embodiment, the measurements of CoR can be conducted continually and automatically with computer 50 continually recording the pre- and post-impact velocities and the repositioning device 60 continually moving the second object 30 back to the initial, pre-impact position to start a new cycle. In this embodiment, enlarged section 110 (shown in FIG. 3) may have an open bottom for the first objects 15 to fall through and collected to be fed back, e.g., by gravity, to launching device 25 to be re-tested. Hence, this embodiment can be operated without user input, once the apparatus is set-up and started.

Additionally, in this embodiment when the first objects 15 are golf balls, the CoR measuring apparatus can also act as a durability tester for golf balls. A single golf ball or a set of golf balls can be repeatedly and automatically impacted against second object 30, or in this case a simulated club, until failure of the golf ball(s) is detected. The golf ball or golf balls are continually fed back to the launching device and the simulated golf club is repositioned to the pre-impacted position automatically after each impact. Advantageously, different clubs, e.g., flexible-face driver, other driver, irons, can be tested to determine the durability of any golf ball with different clubs.

While the above invention has been described with reference to certain preferred embodiments, it should be kept in mind that the scope of the present invention is not limited to these embodiments. One skilled in the art may find variations of these preferred embodiments which, nevertheless, fall within the spirit of the present invention. Additionally, features from any one embodiment may be used singly or in combination with other features from the same embodiment or from other embodiments and still fall within the scope of the invention, whose scope is defined by the claims set forth below.

What is claimed is:

1. A method for testing the coefficient of restitution of a golf ball comprising the steps of:
    positioning an impacted object in an initial stationary position in an enclosure;
    constraining the impacted object to movement within a predetermined path within the enclosure;
    moving an impacting object toward and impacting the impacted object, wherein one of either the impacting object or the impacted object is the golf ball;
    determining the pre-impact velocity of the impacting object;
    determining the post-impact velocity of the impacted object; and
    determining the coefficient of restitution of the golf ball.

2. The method of claim 1, wherein the impacting object is the golf ball, and the impacted object is a simulated golf club.

3. The method of claim 1, wherein the impacting object is a simulated golf club and the impacted object is the golf ball.

4. The method of claim 1, further comprising the step of automatically returning the impacted object to the initial position.

5. A method for testing the durability of a golf ball comprising the steps of:
    (a) positioning an impacted object in an initial position in an enclosure;
    (b) constraining the impacted object to movement within a predetermined path within the enclosure;
    (c) moving an impacting object at a predetermined velocity toward and impacting the impacted object, wherein one of either the impacting object or the impacted object is the golf ball;
    (d) automatically returning the impacted object to the initial position; and
    (e) repeating steps (c) and (d) until failure of the golf ball is noted.

6. The method of claim 5, wherein the impacting object is the golf ball, and the impacted object is a simulated golf club.

7. The method of claim 5, wherein the impacting object is a simulated golf club and the impacted object is the golf ball.

8. The method of claim 5, further comprising the step of providing a launching device to move the impacting object toward the impacted object.

9. The method of claim 8, wherein the impacting object comprises a plurality of golf balls and the impacted object is a simulated golf club.

10. The method of claim 5, wherein step (d) comprises the step of providing a repositioning device to return the impacted object to the initial position.

11. An apparatus for testing golf ball comprising:
an enclosure defining a predetermined path;
an impacted object positioned in an initial position within said predetermined path, wherein the movement of the impacted object after impact is constrained within the predetermined path; and
a launching device configured to launch an impacting object at a predetermined velocity to impact the impacted object, wherein one of either the impacting object or the impacted object is the golf ball.

12. The apparatus of claim 11, wherein the enclosure is connected to a dampening device adapted to retain the impacted object after impact.

13. The apparatus of claim 11, wherein the enclosure defines a plurality of perforations on its surface.

14. The apparatus of claim 11, wherein the other of either the impacting object or the impacted object is a simulated golf club.

15. The apparatus of claim 14, wherein the simulated golf club is hollow and comprises an impacted face.

16. The apparatus of claim 15, wherein the impacted face is flexible.

17. The apparatus of claim 11, wherein the enclosure further comprises a vented section.

18. The apparatus of claim 11, wherein the enclosure is connected to a repositioning device associated with the impacted abject to return the imparted object to the initial position after impact.

19. The apparatus of claim 18, wherein the repositioning device is selected from a group consisting of a rod-and-piston mechanism, a rod-and-rotating wheel mechanism, a pneumatically controlled rod, a magnetic or magnetized sleeve, a spring, an energy storing device, a kinetic-to-potential energy converter, and combination thereof.

20. The apparatus of claim 11, further comprising a first sensor for determining the pre-impact velocity of the impacting object and a second sensor far determining the post-impact velocity of the impacted object.

21. The apparatus of claim 14, wherein the simulated golf club weighs between about 100 grams and about 500 grams.

22. The apparatus of claim 21, wherein the simulated golf club weighs between about 180 grams and about 250 grams.

23. The apparatus of claim 22, wherein the simulated golf club weighs about 200 grams.

* * * * *